United States Patent [19]

Zuest et al.

[11] Patent Number: 4,547,159
[45] Date of Patent: Oct. 15, 1985

[54] SNAP-IN ANCHOR FOR DENTURE

[76] Inventors: Max Zuest, 595 San Fernando, San Diego, Calif. 92106; Paul Zuest, 13531 Orange Blossom La., Poway, Calif. 92064

[21] Appl. No.: 683,478

[22] Filed: Dec. 19, 1984

[51] Int. Cl.$^4$ .............................................. A61C 13/22
[52] U.S. Cl. .................................................... 433/181
[58] Field of Search .............. 433/181, 182, 183, 169, 433/180

[56] References Cited

U.S. PATENT DOCUMENTS

| 866,304 | 9/1907 | Roach | 433/183 |
|---|---|---|---|
| 1,158,732 | 11/1915 | Shaw | 433/180 |
| 1,937,345 | 11/1933 | Jackman | 433/181 |
| 3,787,975 | 1/1974 | Zuest | 433/183 |
| 4,362,509 | 12/1982 | Sulc | 433/169 |

FOREIGN PATENT DOCUMENTS 733478  2/1943  Fed. Rep. of Germany ...... 433/183

Primary Examiner—John J. Wilson
Attorney, Agent, or Firm—Brown, Martin & Haller

[57] ABSTRACT

A snap-in anchor for a denture, including an open-sided sleeve with a socket at one end, which is inset and secured directly in an existing tooth. A snap pin with an enlarged head is embedded in the denture by a retaining lug extending from the pin, the denture being anchored by sliding the pin into the sleeve and snapping the head into the socket. The sleeve has resilient side walls that frictionally grip the entire length of the pin for stability but that allow very limited movement of the denture to accommodate jaw motions.

9 Claims, 7 Drawing Figures

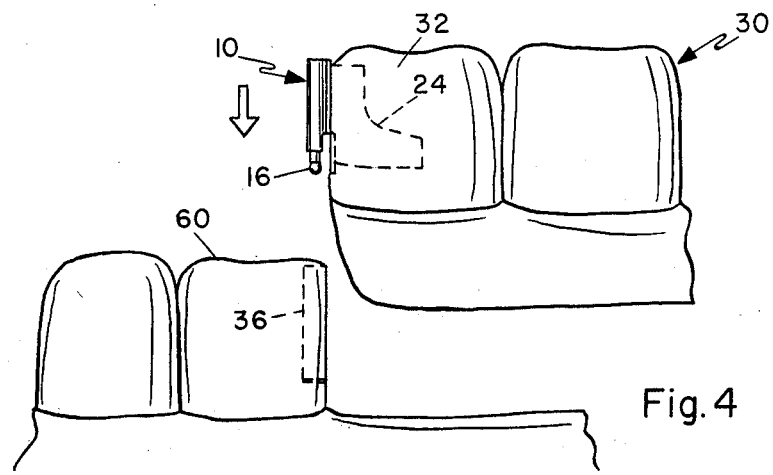
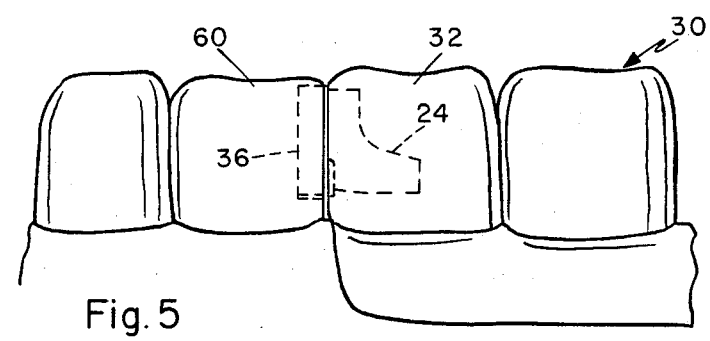
Fig. 4
Fig. 5
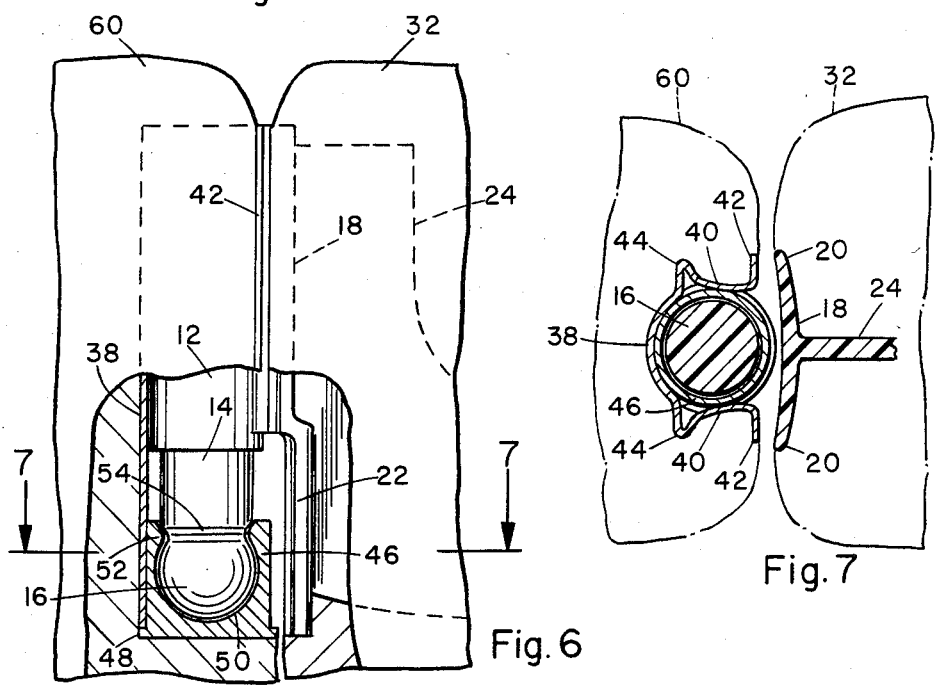
Fig. 6
Fig. 7

SNAP-IN ANCHOR FOR DENTURE

BACKGROUND OF THE INVENTION

Various means have been developed for securing dentures to existing teeth or to the jawbone. In the attachments to existing teeth, the retaining means usually involves a groove or channel formed or inserted in a fabricated ceramic metal crown cemented on the teeth and a matching tongue or pin built into the denture, the tongue sliding into the channel as the denture is seated. Retention is by frictional grip of the tongue in the channel and requires a precision fit for security.

If the fit is close enough for securely holding the denture, the attachment is usually very rigid and does not permit the very slight motion of the denture that is desirable to accommodate a comfortable chewing action. Resilient inserts or cushions have been used but these are subject to wear and require periodic replacement. A typical example of this is described in U.S. Pat. No. 4,362,509 to J. M. Sulc, which has a dovetail-type connection with a plastic insert, the plastic part engaging a very small locking rib that is subject to wear.

SUMMARY OF THE INVENTION

The anchor structure described herein has no inserts, incorporates a positive snap lock and has sufficient resilience to allow a comfortable limited motion of a denture while chewing.

A female element in the form of a metal channel member is inset and bonded directly into an existing tooth and a male element comprising a cylindrical pin is secured to the denture. The pin has a flanged back plate for stability and a retaining tongue that is embedded firmly in the material of the denture, and extended end of the pin having a substantially spherical head. At the base of the channel member is a socket into which the pin head snaps securely.

The channel member grips the pin along its entire length but is provided with protruding longitudinal ribs that allow flexing of the channel under load and will accommodate the necessary slight motion of the denture without losing the locking grip of the ball and socket retainer.

An object of this invention, therefore, is to provide an anchor for a denture that has a positive snap lock, yet that will allow the denture to move with the jaw motions.

Other objects and advantages will be apparent in the following detailed description, taken in conjunction with the accompanying drawings, in which:

FIG. 4 is a side elevation view showing a denture, with the pin element attached, being lowered onto existing teeth containing the channel element;

FIG. 5 is a side elevation view showing the denture locked in place;

FIG. 6 is an enlarged side elevation view, partially cut away, of the snap-in connection; and FIG. 7 is a sectional view taken on Line 7—7 of FIG. 6.

DESCRIPTION OF THE PREFERRED EMBODIMENT

Figure 1:
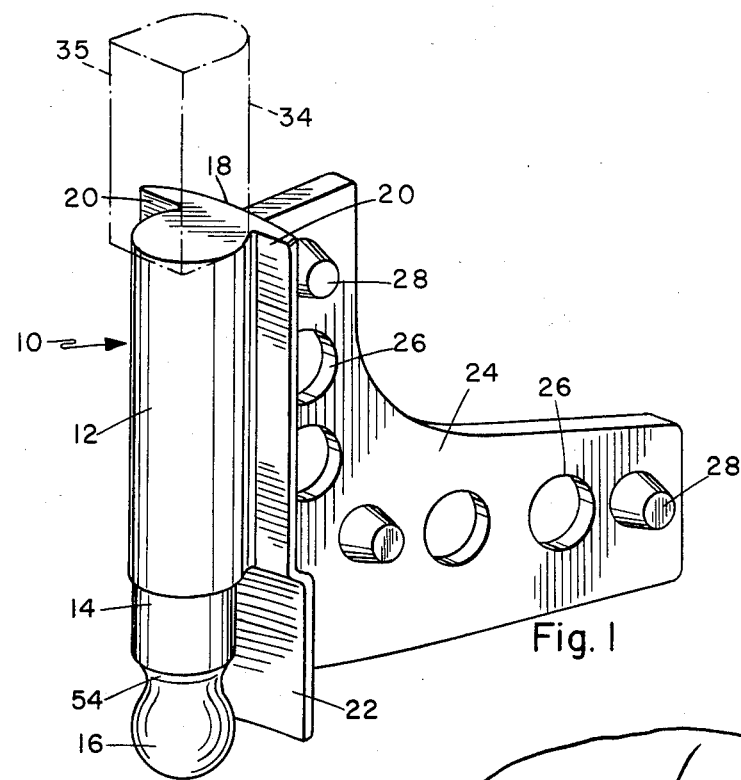
FIG. 1 is a perspective view of the male or pin element.

The male element 10, illustrated in FIG. 1, comprises an elongated cylindrical pin 12 with a reduced diameter end 14 on which is a spherical head or ball 16. A back plate 18 extends along a portion of the pin 12, with oppositely extending flanges 20. In the vicinity of the reduced diameter end 14, the back plate has an offset portion 22 spaced radially from the pin to clear the ball 16.

Projecting from the back plate 18, substantially coplanar with and radial to the longitudinal axis of pin 12, is a retaining tongue 24 having a plurality of holes 26 and projecting studs 28. The tongue 24 is embedded in the denture 30 with the back plate 18 against the face of the end tooth 32, as in FIGS. 4–7. The holes 26 and studs 28 on tongue 24 provide maximum contact and interengagement with the cement or cold compound material of the denture as it sets. When initially installed, the pin 12 has a projecting alignment portion 34 with a flat face 35 to facilitate alignment of the pins on both ends of the denture. After the denture is set, the alignment portion 34 is cut off.

Figure 2:
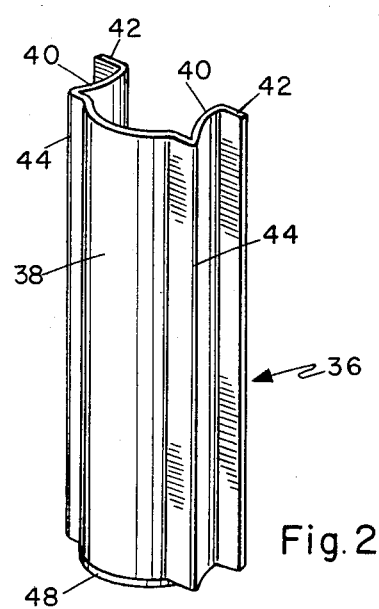
FIG. 2 is a perspective view of the female or channel element.

The female or channel element 36, illustrated in FIG. 2, has a partially cylindrical channel 38 to fit pin 12, the channel having inwardly turned side walls 40 to grip the pin frictionally, the side walls having outwardly projecting flanges 42 on opposite sides of the open side of the channel. At the junction of the side walls 40 with the cylindrical channel 38 are longitudinally extending, outwardly return folded ribs 44. The channel element is made from thin resilient material such as stainless steel, and it is the ribs 44 that provide much of the resilience necessary for the denture to move with the jaw action.

At the lower or base end of the channel element 36 is a socket member 46 that fits inside the channel and has a radially projecting end flange 48 to seat against the end of the channel. Socket member 46 has a socket 50 to receive ball 16, the entry of the socket having a peripheral internal rib 52 to seat in a corresponding undercut groove 54 around the base of the ball at its junction with the pin. The socket member is also of hard-wearing material such as stainless steel and is bonded in the channel by laser welds around end flange 48 and to side walls 40.

Figure 3:
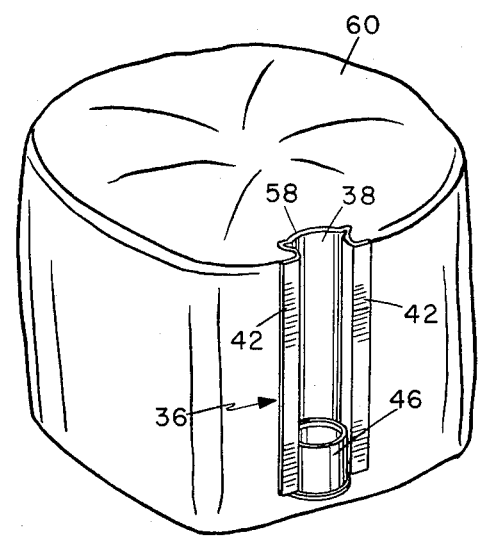
FIG. 3 illustrates the channel element inset in a tooth.

The channel element 36 is inset in a suitably shaped cutout 58 in an existing tooth 60, as in FIG. 3, with the flanges 42 against the end face of the tooth. The channel element is held in the tooth by its divergent configuration of ribs 44 and preferably a minimum of adhesive is used to allow the resilient properties to be effective.

As illustrated in FIG. 4, the denture 30 is lowered into place so that pin 12 fits into the channel element 36 and is pressed down until the ball 16 snaps into socket member 46. The fully seated connection is shown in FIG. 6, where it can be seen that offset portion 22 provides clearance for the socket member 46.

The connection is very secure but can be released when necessary by firm upward pressure on the denture. While locked in place, the denture can move slightly in the vertical and lateral directions to accommodate compression against the gum during chewing. The resilience of the side walls 40 and ribs 44 allow for such movement without relinquishing the grip on the pin and the positive ball and socket snap connection prevents vertical separation of the denture.

It should be understood that the structure illustrated is an example of a particular configuration and that minor changes in specific shapes and proportions can be made without departing from the scope of the invention.

Having described my invention, I now claim:

1. A snap-in anchor for securing a denture to an existing tooth, comprising:
   a male element having an elongated cylindrical pin with a substantially spherical ball on one end;
   a tongue extending radially from said pin for embedding and securing in a denture;
   a female element having an open-sided channel to receive said pin with a frictional sliding fit, said channel having resilient side walls for gripping the pin;
   said female element having a base end with a socket member secured therein, said socket member having a socket to receive said ball with a snap fit;
   and said female element having means for retention in an existing tooth.

2. A snap-in anchor according to claim 1, wherein said channel has a partially cylindrical portion to fit said pin, said side walls being inwardly turned and having outwardly turned flanges on opposite sides of the open channel side to seat against a face of the existing tooth.

3. A snap-in anchor according to claim 2, wherein said female element is of thin resilient sheet material and has longitudinal, outwardly return folded ribs at the junction of said partially cylindrical portion and said side walls.

4. A snap-in anchor according to claim 3, wherein said socket member fits closely in and is bonded to the base end of said female element.

5. A snap-in anchor according to claim 1, wherein said pin has a back plate with oppositely projecting flanges to seat against a face of the denture, said back plate having an offset portion spaced radially from said ball to clear said socket member in the engaged position.

6. A snap-in anchor according to claim 5, wherein said pin has a removable alignment extension on the end opposite said ball, said extension having a flat portion for an alignment reference.

7. A snap-in anchor according to claim 5, wherein said tongue has a plurality of holes therein and studs projecting therefrom for adhesive retention in the denture.

8. A snap-in anchor for securing a denture to an existing tooth, comprising:
   a male element having an elongated cylindrical pin with a substantially spherical ball on one end;
   said pin having a longitudinally extending back plate with flanges protruding on opposite sides to seat against a face of the denture;
   a tongue extending from said back plate radial to the pin for embedding and securing in the denture;
   a female element having an open-sided channel with a partially cylindrical portion to receive said pin and inwardly turned side walls to frictionally grip the pin;
   said female element having a base end with a socket member therein, the socket member having a socket for receiving said ball with a snap action; and
   said side walls having outwardly turned flanges to seat on a face of the existing tooth when the female element is inset therein.

9. A snap-in anchor according to claim 8, wherein said back plate has an offset portion spaced form said ball to clear said clip and socket member in the engaged position.

* * * * *